United States Patent [19]

Muramatsu et al.

[11] 4,348,410

[45] Sep. 7, 1982

[54] CYCLOHEXANE CARBOXYLIC ACID DERIVATIVES

[75] Inventors: Mutsumi Muramatsu; Toshio Satoh, both of Tokushima; Yukio Yanagimoto, Osaka; Tadami Shinuchi, Kyoto; Toshio Nakajima, Fujimi; Isao Nakajima, Toyonaka, all of Japan

[73] Assignees: Nippon Chemiphar Co., Ltd., Tokyo; Teikoku Chemical Industry Co., Ltd., Osaka, both of Japan

[21] Appl. No.: 186,849

[22] Filed: Sep. 15, 1980

[30] Foreign Application Priority Data

Sep. 20, 1979 [JP] Japan .................................. 54-120142
Dec. 26, 1979 [JP] Japan .................................. 54-168271
Dec. 26, 1979 [JP] Japan .................................. 54-168272

[51] Int. Cl.$^3$ .................... A61K 31/24; A61K 31/215; C07C 69/773; C07C 69/614

[52] U.S. Cl. ..................................... 424/309; 424/305; 560/66; 560/55; 560/125; 546/301; 560/37; 560/38

[58] Field of Search ................ 424/309, 305; 560/66, 560/55, 125, 37, 38

[56] References Cited

U.S. PATENT DOCUMENTS 4,147,876  4/1979  Kamada et al. ...................... 560/37

*Primary Examiner*—John M. Ford
*Attorney, Agent, or Firm*—Oblon, Fisher, Spivak, McClelland & Maier

[57] ABSTRACT

A compound of the formula:

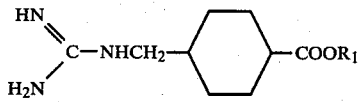

wherein $R_1$ represents a vanilyl, napthyl, pyridyl or α-tocopheryl group, or a group of the formula,

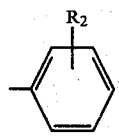

wherein $R_2$ represents a hydrogen atom, a lower alkoxy, formyl, lower alkanoyl or phenyl group, or a group of the formula —$(CH_2)_n COOR_3$, wherein $R_3$ represents a hydrogen atom, a lower alkyl, phenyl, benzyl, anisyl or lower alkoxycarbonylmethyl group, and n represents an integer of 0 to 2, or a pharmaceutically acceptable salt thereof is effective for use as an anti-ulcer agent.

11 Claims, No Drawings

CYCLOHEXANE CARBOXYLIC ACID DERIVATIVES

BACKGROUND OF THE INVENTION

1. Field of the Invention

This invention relates to novel cyclohexane carboxylic acid derivatives, a process for producing the same and a pharmaceutical composition containing the same.

2. Description of the Prior Art

Tranexamic acid (trans-4-aminomethylcyclohexane carboxylic acid) is a cyclohexane carboxylic acid derivative, and is known to possess excellent anti-plasmin effects. The esters of tranexamic acid are also known to possess excellent anti-plasmin effects (A. Okano et al, J. Med. Chem., Vol. 15, No. 3, 247 (1972)). However, it was reported that 4-guanidinomethylcyclohexanecarboxylic acid exhibited little anti-plasmin effects (ibid.).

A variety of cyclohexane derivatives has now been studied, resulting in the present discovery.

SUMMARY OF THE INVENTION

One object of the present invention is to provide novel cyclohexane carboxylic acid derivatives which exhibit strong inhibitory effects on protease, anti-ulcer effects, anti-histamine effects, anti-inflammatory effects and anti-allergic effects.

It is another object of the present invention to provide a process for producing these novel cyclohexane carboxylic acid derivatives.

Further, it is another object of the present invention to provide a cyclohexane carboxylic acid derivative useful as an anti-ulcer agent.

These and other objects of the invention as hereinafter will become more readily apparent can be attained by the discovery of compounds of the formula (I):

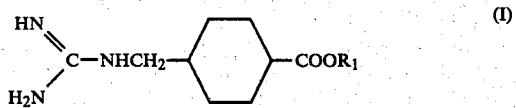
(I)

wherein $R_1$ represents vanilyl, naphthyl, pyridyl, α-tocopheryl a group of the formula,

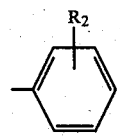

wherein $R_2$ represents hydrogen, lower akoxy, formyl, lower alkanoyl, phenyl or a group of the formula $-(CH_2)nCOOR_3$, wherein $R_3$ represents hydrogen, lower alkyl, phenyl, benzyl, anisyl or lower alkoxycarbonylmethyl, and n represents an integer of 0 to 2. These derivatives and pharmaceutically acceptable salts thereof have been found to possess excellent inhibitory effects on protease, anti-ulcer effects and anti-histamine effects, anti-inflammatory effects and anti-allergic effects. Particularly, the compounds of the formula (II):

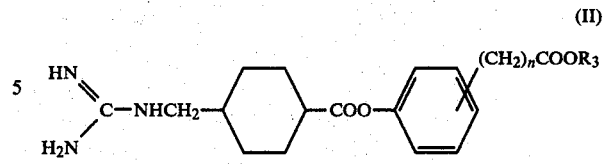
(II)

wherein $R_3$ and n are the same as defined above, have been found to possess excellent inhibitory effects on gastric secretion, preventive and healing effects on various gastric and duodenal ulcers.

DETAILED DESCRIPTION OF THE PREFERRED EMBODIMENTS

The ester residues $R_1$ of the present compounds of the formula (I) may be vaniyl, naphthyl, pyridyl, α-tocopheryl or a group of the formula

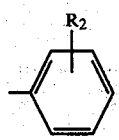

Suitable naphthyl groups include α-naphthyl or β-naphthyl groups. Suitable pyridyl groups include 2-pyridyl, 3-pyridyl or 4-pyridyl groups. Suitable groups of the formula

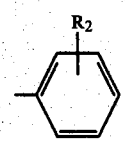

include phenyl, methoxyphenyl, ethoxyphenyl, propoxyphenyl, formylphenyl, acetylphenyl, propanoylphenyl, butyrylphenyl, biphenyl or a group of the formula

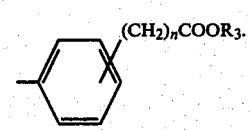

Suitable groups of the formula

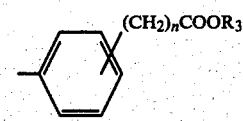

include hydroxycarbonylphenyl, methoxycarbonylphenyl, ethoxycarbonylphenyl, t-butoxycarbonylphenyl, phenoxycarbonylphenyl, benzyloxycarbonylphenyl, anisyloxycarbonylphenyl, (ethoxycarbonyl)methoxycarbonylphenyl, hydroxycarbonylmethylphenyl, methoxycarbonylmethylphenyl, ethoxycarbonylmethylphenyl, t-butoxycarbonylmethylphenyl, phenoxycarbonylmethylphenyl, benzyloxycarbonylmethylphenyl, hydroxycarbonylethylphenyl, ethoxycarbonylethylphenyl, (ethoxycarbonyl)ethoxycarbonylethylphenyl, phenoxycarbonylethylphenyl, benzyloxycarbonylethylphenyl, anisyloxycarbonylethylphenyl or the like.

Compounds of the formula (I) may be eithr the cis- or trans-isomer. Particularly preferable is the trans isomer.

The pharmaceutically acceptable salts of the present compounds are the acid addition salts formed from hydrochloric acid, sulfuric acid, phosphoric acid, hydrobromic acid, acetic acid, lactic acid, maleic acid, fumaric acid, tartaric acid, citric acid, methanesulfonic acid, p-toluenesulfonic acid or the like.

According to the present invention, the compounds of the formula (I) are produced by reacting 4-guanidinomethyl cyclohexane carboxylic acid or a reactive derivative thereof with a compound of the formula (III):

$$R'_1-OH \quad (III)$$

wherein $R'_1$ represents vanilyl, naphthyl, pyridyl, α-tocopheryl or a group of the formula $$\underset{R'_2}{\bigodot},$$

wherein $R_2'$ represents hydrogen, lower alkoxy, formyl, lower alkanoyl, phenyl or a group of the formula $-(CH_2)_nCOOR_3'$, wherein $R_3'$ represents lower alkyl, phenyl, benzyl, anisyl, lower alkoxycarbonylmethyl and n represents an integer of 0 to 2; and when desired, removing the benzyl, anisyl or lower alkoxycarbonylmethyl group from the product.

Suitable reactive derivatives of 4-guanidinomethylcyclohexanecarboxylic acid include the acid halides, for example, acid chloride, acid bromide or the like, and mixed anhydrides using ethyl chlorformate, butyl chlorformate or the like. Acid halides are produced by reacting 4-guanidinomethylcyclohexanecarboxylic acid with halogenation reagents such as thionyl chloride and thionyl bromide at a temperature of from room temperature to the boiling point of the halogenation reagent. The thus obtained acid halides are reacted with the compounds of the formula (III) to give the present compounds. This reaction is carried out by stirring at a temperature of from room temperature to the boiling point of the solvent for 1 to 40 hours. Suitable solvents which may be used include dimethylformamide, dimethylacetamide, pyridine, dichloromethane, dichloroethane, chloroform, acetonitrile or the like. Use of an acid-binding agent, e.g., thiethylamine, dimethylaniline or pyridine is sometimes recommendable.

When 4-guanidinomethylcyclohexanecarboxylic acid is reacted directly without conversion to reactive intermediate thereof, the reaction is preferably carried out in the presence of a condensing agent, for example, carbodiimide such as dicyclohexylcarbodiimide or 1-ethyl-3-(3'-dimethylaminopropyl)carbodiimide hydrochloride, sulfuric acid-boric acid, carbodiimidazole, sufodiimidazole, or Lewis acid such as phosphorousoxychloride or boron trifluoride. The reaction is carried out with a solvent, for example, toluene, xylene or dimethylformamide, a solvent as mentioned above, or mixtures thereof at a temperature of from room temperature to the boiling point of the solvent.

The compounds of the formula (I) wherein $R_3$ represents a hydrogen atom are produced by hydrogenating the compounds of the formula (I) wherein $R_3$ represents a benzyl or anisyl group in the presence of a catalyst, for example, palladium. These compounds may also be produced by hydrolyzing the compounds of the formula (I) wherein $R_3$ represents a butyl or lower alkoycarbonylmethyl group in the presence of a catalyst, for example, trifluoroacetic acid or hydrochloric-acetic acid.

Compounds of the formula (IV)

$$\underset{H_2N}{\overset{HN}{\diagdown}}C-NHCH_2-\bigcirc-COO-\bigcirc^{(CH_2)COOR'_3} \quad (IV)$$

wherein $R_3'$ and n are the same as defined above, may also be produced by reacting the compounds of the formula (V)

$$\underset{H_2N}{\overset{HN}{\diagdown}}C-NHCH_2-\bigcirc-COO-\bigcirc^{(CH_2)COOH} \quad (V)$$

wherein n is the same as defined above, or a reactive derivative thereof, with a compound of the formula (VI)

$$R_3-OH \quad (VI)$$

wherein $R_3'$ is the same as defined above.

The reaction is carried out by the same procedure of the above mentioned esterification.

The thus obtained compounds of the formula (I) are then isolated by conventional techniques.

Usually, it is best to recover the present compounds in the form of their acid addition salts as above mentioned.

The compounds of the formula (I) may contain crystal water in equimolar amounts.

The thus obtained compounds of the formula (I) have an excellent range of pharmaceutical activity. That is, the present compounds will exhibit excellent inhibitory effects on protease, such as trypsin, chymotrypsin, thrombin or urokinase. The present compounds also exhibit excellent anti-ulcer effects. They can thus be used as an excellent preventive or for healing ulcer models in rats such as Shay ulcers, stress ulcers, indomethacin ulcers, acetic acid-induced ulcers, cysteamine ulcers or histamine ulcers.

These compounds were found to strongly inhibit the volume of the gastric secretion, the acidity of the gastric juices and peptic activity. Moreover, these effects appear to be quite long lasting. Experiments of acute and subacute toxicity confirmed that the present compounds have a low degree of toxicity. Particularly, the compounds of the formula (II) exhibit excellent anti-ulcer effects and appear to be remarkably safe.

Compounds of the present invention also exhibit anti-histamine effects, anti-inflammatory effects and anti-allergic effects (passive cutaneous anaphylaxis tests.

The compounds of the formula (I) have excellent inhibitory effects on protease. The inhibitory effects were determined by the following methods:

(1) Inhibitory Effects on Trypsin:

Inhibitory effects of the compounds on trypsin were determined according to the method described by M. Muramatsu et al (The Journal of Biochemistry, Volume 58, 214 (1965)). In particular, inhibitory effects of the compounds on hydrolysis of p-tosylarginine methyl ester by trypsin were examined (incubated at 37° C. for 10 minutes).

(2) Inhibitory Effects on Chymotrypsin:

Inhibitory effects on the compounds of chymotrypsin were determined according to the method described by M. Muramatsu (The Journal of Biochemistry, Volume 62 (4), 408 (1967)). In particular, inhibitory effects of the compounds on hydrolysis of N-acetyl-L-tyrosine ethyl ester by chymotrypsin were examined (incubated at 37° C. for 10 minutes).

(3) Inhibitory Effects on Thrombin:

Inhibitory effects of the compounds on thrombin were determined according to the method described by M. Muramatsu et al (The Journal of Biochemistry, Volume 65 (1), 17 (1969)). In particular, inhibitory effects of the compounds on hydrolysis of p-tosylarginine methyl ester by thrombin were examined (incubated at 37° C. for 10 minutes).

(4) Inhibitory Effects on Urokinase:

Inhibitory effects of the compounds on urokinase were determined according to the method described by A. J. Joeson et al (Throm. Diath Haemorrh. 21, 259–272 (1969)). In particular, inhibitory effects of the compounds on hydrolysis of N-acetylglycyl lysine methyl ester by urokinase were determined (incubated at 37° C. for 10 minutes).

The results obtained are shown in Table 1.

TABLE 1

| Test | INHIBITORY EFFECTS ON PROTEASE Inhibition (%) | | | |
|---|---|---|---|---|
| Compound | Trypsin | Chymotrypsin | Thrombin | Urokinase |
| Compound 1 | 79 | 100 | 37 | 32 |
| Compound 2 | 61 | 100 | 51 | 72 |
| Compound 3 | 42 | 48 | 30 | 52 |
| Compound 4 | 22 | 28 | 35 | 84 |
| Compound 5 | 38 | 90 | 34 | 35 |
| Compound 6 | 25 | 70 | 39 | 50 |
| Compound 7 | 23 | 70 | 32 | 67 |
| Compound 8 | 51 | 20 | 43 | 55 |
| Compound 9 | 28 | 60 | 29 | 50 |
| Compound A | 65 | 0 | 30 | 32 |

Compound 1: 2'-benzyloxycarbonylphenyl trans-4-guanidinomethylcyclohexanecarboxylate hydrochloride
Compound 2: 2'-methoxy-4'-formylphenyl trans-4-guanidinomethylcyclohexanecarboxylate hydrochloride
Compound 3: phenyl trans-4-guanidinomethylcyclohexanecarboxylate hydrochloride
Compound 4: 2'-ethoxyphenyl trans-4-guanidinomethylcyclohexanecarboxylate hydrochloride
Compound 5: 2'-phenoxycarbonylphenyl trans-4-guanidinomethylcyclohexanecarboxylate hydrochloride
Compound 6: 4'-ethoxycarbonylphenyl trans-4-guanidinomethylcyclohexanecarboxylate hydrochloride
Compound 7: 3'-pyridyl trans-4-guanidinomethylcyclohexanecarboxylate hydrochloride
Compound 8: 4'-(2''-ethoxycarbonylethyl)phenyl trans-4-guanidinomethylcyclohexanecarboxylate hydrochloride
Compound 9: 2'-ethoxycarbonylphenyl trans-4-guanidinomethylcyclohexanecarboxylate hydrochloride
Compound A: 4'-(2''-hydroxycarbonylethyl)phenyl trans-4-aminomethylcyclohexanecarboxylate hydrochloride (described in J. Med. Chem., Vol. 15, No. 3, 247 (1972))

1. Shay Ulcers

Male Sprague-Dawley strain rats, weighing 160–180 g were deprived of food but allowed free access to water for 20 hours prior to experiment. Under ether anesthesia, the abdomen was incised and the pylorus was ligated as described by Shay et al (Gastroenterology, 5, 43 (1945)).

The rats were sacrificed 18 hours later by an overdose of ether and the stomach removed. The stomach was incised along the greater curvature and the surface area of each lesion in forestomach was measured by the naked eye. The lesion was arbitrarily graded into 6 degrees as an ulcer index according to the method of Adami et al (arch. int. Pharmacodyn., 147, 113–145 (1964)) as follows:

0 = no lesion
1 = hemorrhagic suffusion
2 = 1–5 small ulcers (<3 mm)
3 = many small ulcers (more than 5) or 1 ulcer of marked size
4 = many ulcers of marked size
5 = perforated ulcer The test drugs were given intraperitoneally, immediately after pylorus ligation. The results obtained are shown in Table 2.

TABLE 2

| Test | Dose | SHAY ULCERS Ulcer Grade | | | | | | |
|---|---|---|---|---|---|---|---|---|
| Compound | (mg/kg) | 0 | 1 | 2 | 3 | 4 | 5 | Total |
| Control | — | 0 | 1 | 0 | 2 | 2 | 5 | 10 |
| Compound 1 | 300 | 7 | 0 | 0 | 0 | 0 | 0 | 7 |
| Compound 1 | 150 | 10 | 0 | 0 | 0 | 0 | 0 | 10 |
| Compound 1 | 75 | 8 | 0 | 2 | 0 | 0 | 0 | 10 |
| Compound 3 | 400 | 11 | 4 | 5 | 0 | 0 | 0 | 20 |
| Compound 8 | 200 | 4 | 2 | 2 | 1 | 1 | 0 | 10 |
| Compound B | 12.5 | 2 | 1 | 0 | 1 | 3 | 3 | 10 |
| Compound A | 300 | 6 | 0 | 0 | 1 | 2 | 1 | 10 |
| Compound A | 150 | 2 | 0 | 3 | 1 | 4 | 0 | 10 |

Compound B: atropine sulfate
Compound 1, Compound 3, Compound 8 and Compound A are the same as defined above.

2. Acetic Acid Ulcers

Male Sprague-Dawley strain rats, weighing about 200 g were used. Under ether anesthesia 10% acetic acid solution (0.05 ml) was injected carefully between the serous membrane and the muscle near the pylorus, and the abdomen was closed. Thereafter, the animals were maintained under conditions and administered 1 ml/100 g of each test drug dissolved or suspended in 0.5% carboxymethylcellulose solution p.o. daily×10 starting from the next day of the operation. On the 11th day, the rats were sacrificed under ether anesthesia, and the stomachs were removed. The area of the ulcer was measured and graded into 5 degrees as an ulcer index according to the following method:

| Ulcer Index | The Ulcer Area |
|---|---|
| 1 | 0–10 mm² |
| 2 | 11–20 mm² |
| 3 | 21–30 mm² |
| 4 | 31–40 mm² |
| 5 | >40 mm² |

The results obtained are shown in Table 3.

TABLE 3

| Test | Dose | ACETIC ACID ULCERS Ulcer Grade | | | | | |
|---|---|---|---|---|---|---|---|
| Compound | (mg/kg) | 1 | 2 | 3 | 4 | 5 | Total |
| Control | — | 0 | 0 | 3 | 3 | 7 | 13 |
| Compound 1 | 500 | 16 | 2 | 0 | 0 | 0 | 18 |
| Compound 1 | 250 | 14 | 1 | 1 | 0 | 0 | 16 |
| Compound 1 | 125 | 15 | 1 | 2 | 0 | 0 | 18 |

TABLE 3-continued

ACETIC ACID ULCERS

| Test Compound | Dose (mg/kg) | Ulcer Grade 1 | 2 | 3 | 4 | 5 | Total |
|---|---|---|---|---|---|---|---|
| Compound 2 | 500 | 12 | 3 | 2 | 0 | 1 | 18 |
| Compound 2 | 250 | 14 | 0 | 3 | 1 | 0 | 18 |
| Compound 2 | 125 | 9 | 1 | 2 | 2 | 1 | 15 |
| Compound 8 | 300 | 4 | 3 | 1 | 0 | 0 | 8 |
| Compound 9 | 500 | 12 | 2 | 1 | 0 | 0 | 15 |
| Compound 9 | 250 | 11 | 2 | 1 | 0 | 0 | 14 |
| Compound 9 | 125 | 11 | 3 | 1 | 1 | 1 | 17 |
| Compound 10 | 500 | 4 | 3 | 1 | 0 | 0 | 8 |
| Compound 10 | 300 | 4 | 2 | 1 | 0 | 2 | 9 |
| Compound A | 500 | 7 | 6 | 1 | 0 | 1 | 15 |
| Compound A | 300 | 2 | 2 | 2 | 1 | 1 | 8 |
| Compound A | 250 | 4 | 8 | 3 | 2 | 0 | 17 |

Compound 10: 2'-hydroxycarbonylphenyl trans-4-guanidinomethylcyclohexanecarboxylate hydrochloride
Compound 1, Compound 2, Compound 8, Compound 9 and Compound A are the same as defined above.

3. Duodenal Ulcers (Cysteamine-Induced)

Female Sprague-Dawley strain rats, weighing about 200 g were deprived of food for 24 hours prior to experiment. Cysteamine 400 mg/kg was given subcutaneously once to the rats. The animals were provided food and libitum from the 7 hours later. The test drug was given orally as aqueous suspension after 7 hours, the administration of cysteamine, then daily×4. On the next morning of the last administration, the animals were sacrificed under ether anesthesia. The ulcer area ($mm^2$) was measured and described as ulcer index.

The results obtained are shown in Table 4.

TABLE 4

CYSTEAMINE-INDUCED ULCERS

| Test Compounds | Dose (mg/kg) | Number of Rats | Ulcer Index ($mm^2$) | Inhibition (%) |
|---|---|---|---|---|
| Control | — | 7 | 80.7 ± 4.3 | — |
| Compound 1 | 500 | 6 | 11.7 ± 3.6 | 85.5 |
| Compound 1 | 250 | 6 | 22.5 ± 3.9 | 72.1 |

Compound 1 is the same as defined above.

4. The Influence to the Gastric Secretion

Male Sprague-Dawley strain rats, weighing 160–180 g were deprived of food but allowed free access to water for 20 hours prior to experiment. Under ether anesthesion, the abdomen was incised and the pylorus was ligated as described by Shay et al (Gastroenterology, 5, 43 (1945)). The test drug was given intraperitoneally immediately after pylorus ligation. The rats were sacrificed 3, 6 and 12 hours later and the stomachs removed. The gastric juice was collected and analyzed for volume. Then the gastric juice was centrifuged at 1300 g for 10 minutes at room temperature to give the supernatant. The total acidity and peptic activity of the supernatant were determined. Total acidity was determined by titrating with 0.01 N NaOH. Peptic activity was determined according to the method described by Anson et al (J. Gen. Physiol., 22, 79–89 (1938)). The results are shown in Tables 5–7. Total acidity is shown as the titration volume (ml) and peptic activity is shown as the corresponding weight (mg) to crystal pepsin.

TABLE 5

(3 Hours After Trial)

| | | | Gastric Contents | | | | | |
|---|---|---|---|---|---|---|---|---|
| Test Compounds | Dose (mg/kg) | Number of Rats | Volume (ml) | % change | Titratable Acid Output (μEg) | % change | Titratable Pepsin Output (mg) | % change |
| Control | — | 5 | 2.9 ± 0.2 | — | 82.6 ± 10.6 | — | 5.8 ± 0.9 | — |
| Compound 1 | 300 | 5 | 0.5 ± 0.2 | 82.8 | 4.6 ± 3.3 | 94.4 | 0.9 ± 0.6 | 84.5 |
| Compound 1 | 150 | 5 | 0.7 ± 0.3 | 75.9 | 9.8 ± 3.3 | 88.1 | 1.4 ± 0.7 | 75.9 |
| Compound 1 | 75 | 5 | 2.6 ± 0.4 | 10.3 | 39.2 ± 11.6 | 52.5 | 5.7 ± 1.5 | 1.7 |
| Compound B | 12.5 | 5 | 1.2 ± 0.2 | 58.6 | 17.7 ± 7.7 | 78.6 | 3.3 ± 0.9 | 43.1 |
| Compound C | 300 | 5 | 1.4 ± 0.3 | 51.7 | 22.2 ± 11.5 | 73.1 | 3.1 ± 0.8 | 46.6 |
| Compound C | 150 | 5 | 2.1 ± 0.3 | 27.6 | 4.0 ± 4.0 | 95.2 | 5.6 ± 0.5 | 3.4 |
| Compound C | 75 | 5 | 3.2 ± 0.4 | −10.3 | 44.7 ± 12.6 | 45.9 | 9.6 ± 2.3 | −65.5 |

TABLE 6

(6 Hours After Trial)

| | | | Gastric Contents | | | | | |
|---|---|---|---|---|---|---|---|---|
| Test Compounds | Dose (mg/kg) | Number of Rats | Volume (ml) | % change | Titratable Acid Output (μEq) | % change | Titratable Pepsin Output (mg) | % change |
| Control | | 5 | 6.1 ± 0.6 | — | 381.9 ± 67.5 | — | 21.7 ± 3.4 | — |
| Compound 1 | 300 | 5 | 1.5 ± 0.3 | 75.4 | 70.4 ± 30.4 | 81.6 | 3.5 ± 1.4 | 83.9 |
| | 150 | 5 | 1.5 ± 0.3 | 75.4 | 85.3 ± 49.4 | 77.7 | 4.7 ± 1.1 | 78.3 |
| | 75 | 5 | 4.2 ± 0.6 | 31.1 | 259.8 ± 61.8 | 32.0 | 13.9 ± 3.0 | 35.9 |
| Compound B | 12.5 | 5 | 2.7 ± 0.6 | 55.7 | 171.6 ± 50.0 | 55.1 | 9.7 ± 1.6 | 55.3 |
| Compound C | 300 | 5 | 2.1 ± 0.7 | 65.6 | 45.3 ± 26.3 88.1 | 8.9 ± 1.7 | 59.0 | |
| | 150 | 5 | 4.8 ± 0.5 | 21.3 | 290.6 ± 70.5 | 23.9 | 18.7 ± 2.2 | 13.8 |
| | 75 | 5 | 4.3 ± 0.5 | 29.5 | 220.3 ± 30.4 | 42.3 | 15.2 ± 1.5 | 30.0 |

Compound 1, B and C are the same as defined above.

TABLE 7

| Test Compounds | Dose (mg/kg) | Number of Rats | Gastric Contents (12 Hours After Trial) | | | | | |
|---|---|---|---|---|---|---|---|---|
| | | | Volume | | Titratable Acid Output | | Titratable Pepsin Output | |
| | | | (ml) | % change | (μEq) | % change | (mg) | % change |
| Control | | 5 | 13.5 ± 1.8 | — | 820.6 ± 100.0 | — | 58.0 ± 9.8 | — |
| Compound 1 | 300 | 5 | 3.6 ± 0.6 | 73.3 | 258.4 ± 66.9 | 68.5 | 14.0 ± 2.4 | 75.9 |
| | 150 | 5 | 6.3 ± 0.9 | 53.3 | 387.3 ± 79.3 | 52.8 | 24.0 ± 4.2 | 58.6 |
| | 75 | 5 | 5.2 ± 2.1 | 61.5 | 394.6 ± 136.5 | 51.9 | 27.3 ± 8.6 | 52.9 |
| Compound B | 12.5 | 5 | 8.1 ± 0.4 | 40.0 | 617.1 ± 48.0 | 24.8 | 34.2 ± 1.4 | 41.0 |
| Compound C | 300 | 5 | 8.2 ± 0.4 | 39.3 | 597.0 ± 31.4 | 27.2 | 34.2 ± 21.9 | 41.0 |
| | 150 | 5 | 9.5 ± 0.4 | 29.6 | 638.0 ± 22.7 | 22.3 | 41.2 ± 2.0 | 29.0 |
| | 75 | 5 | 12.0 ± 0.9 | 11.1 | 746.6 ± 52.8 | 9.1 | 45.9 ± 3.6 | 20.9 |

Compound 1, B and C are the same as defined above.

The toxicity of the typical compound of the present compounds is described in the following:

1. Acute Toxicity.

Normal ICR strain mice (male: 25~27 g, female: 22~24 g) were used. The test drugs were given orally using gastric sonde. Animals were observed for 7 days. The LD50 value was calculated by the Probit method (C.I. Bliss). The results obtained are shown in Table 8.

TABLE 8

| Test Compounds | LD50(mg/kg) | |
|---|---|---|
| | Female | male |
| Compound 1 | >8000 | 7600 |

Compound 1 is the same as defined above.

2. Sub-acute Toxicity

Sprague-Dawley strain rats, weighing about 150 g were used. The dose was administered once a day, one month. Dosages were set at 4 levels: 40 mg/kg, 130 mg/kg, 400 mg/kg, 1300 mg/kg of 2'-benzyloxycarbonylphenyl trans-4-guanidinomethylcyclohexanecarboxylate hydrochloride. The following items were observed.

(1) Observations of general symtoms, body weight, food-intake and water-intake.
(2) Hematological examinations
(3) Serum-biochemical examinations
(4) Organ weight
(5) Histopathological examinations As the results, 4 rats died only at the highest dose (1300 mg/kg), but toxic lesions were not observed at the other doses.

Certain compounds of the formula (I) exhibit anti-histamin effects. For example, 1~5 μg of phenyl trans-4-guanidinomethylcyclohexanecarboxylate hydrochloride inhibited completely the contraction of the ileum of a guinea pig induced by $10^{-6}$ g/ml of histamin dihydrochloride 0.50 μg of phenyl trans-4-guanidinomethylcyclohexanecarboxylate hydrochloride inhibited completely the contraction of the ileum of a guinea pig, sensitized with egg albumin, when the compound was given with 250 μg/ml egg albumin as antigen. Further, phenyl trans-4-guanidinomethylcyclohexanecarboxylate inhibited carrageenin-induced inflammation (Wister strain rats, I.P., ED50=about 200 mg/kg). When the compounds of the present invention are used as anti-ulcer agents, particularly prefered are the compounds having the formula (II). These compounds exhibit both oral and parenteral activities, but, of course, oral would be the preferable mode of administration. Oral administration can be made by capsule, tablet, powder or granule. In the dosage form, the active compounds are admixed with at least one inert diluent, such as lactose, corn starch, crystalline cellulose; a lubricant, such as magnecium stearate; a binder such as hydroxy propylcellose; a coloring material; perfumery; sweetening agent; or the like.

The dosages of the compounds of this invention in various compositions actually utilized may be varied. However, it is necessary that the amount of the compounds be such that two suitable dosage forms are attained. Any selected dosage depends upon the desired therapeutic effect, administration route and treatment duration. Such dosage lies, in general, in a range from 50~1500 mg/day. This invention is illustrated in further detail with reference to certain specific Examples, which are presented herein for purposes of illustration only and are not to be construed as necessarily limiting of the invention.

EXAMPLE 1

Vitamin E trans-4-guanidinomethylcyclohexanecarboxylate hydrochloride

A suspension of trans-4-guanidinomethylcyclohexanecarboxylic acid hydrochloride (11.8 g), Vitamin E (17.2 g) and dicyclohexylcarbodiimide (12.4 g) in pyridine (150 ml) was stirred at room temperature for 30 hours. After removal of insoluble materials by filtration, the filtrate was evaporated to dryness and the residual solid was treated with a mixture of 0.1 N-hydrochloric acid (200 ml) and ethylacetate (100 ml) for 1 hour. The insoluble materials were removed. The organic layer was filtered, concentrated by filtration, and ether also added to furnish a pale yellow crystal, Vitamin E trans-4-guanidinomethylcyclohexanecarboxylate hydrochloride (16.1 g, 62.1%), m.p. 183°-186° C. IR: $\nu_{max}$(cm$^{-1}$) 1740 (C=O), Analysis: Found: C, 70.62, H, 10.45, N, 6.29, $C_{38}H_{65}N_3O_3 \cdot HCl$ requires: C, 70.39, H, 10.26, N, 6.48.

0.1 mM of this compound inhibited about 50% hydrolytic activity by thrombin and trypsin.

EXAMPLE 2

4'-(2''-Benzyloxycarbonylethyl)phenyl trans-4-guanidinomethylcyclohexanecarboxylate hydrochloride A suspension of trans-4-guanidinomethylcyclohexanecarboxylic acid hydrochloride (7.1 g), benzyl 4-hydroxyphenylpropionate (8.5 g) and dicyclohexylcarbodiimide (7.2 g) in pyridine (75 ml) was stirred at 25° C. for 15 hours. After removal of insoluble materials by filtration, the filtrate was concentrated under reduced pressure. The residue was treated with a mixture of 0.1 N-hydrochloric acid (100 ml) and ethyacetate (50 ml), the resulting solid was removed by filtration. The organic layer was filtered, concentrated and the residual gummy materials were treated with ether and stirred to furnish white crystals which on recrystallization from methanol-ether, gave 4'-(2''-benzyloxycarbonylethyl)phenyl trans-4-guanidinomethylcyclohexanecarboxylate hydrochloride (13.1 g, 92.1%), m.p. 77°-80° C.

IR: $\nu_{max}$(cm$^{-1}$) 1745, 1725 (C=O)

Analysis: Found: C, 62.98, H, 6.65, N, 9.04. $C_{25}H_{31}N_3O_4$·HCl requires: C, 63.55, H, 6.80, N, 8.86.

EXAMPLE 3

4'-(2''-Ethoxycarbonylethyl)phenyl trans-4-guanidinomethylcyclohexanecarboxylate hydrochloride A suspension of trans-4-guanidinomethylcyclohexanecarboxylic acid hydrochloride (11.8 g), ethyl 4-hydroxyphenylpropionate (10.7 g) and dicyclohexycarbodiimide (11.4 g) in pyridine (150 ml) was stirred at 25° C. for 15 hours. After removal of insoluble materials by filtration, the filtrate was evaporated. The residue was treated with 1 N hydrochloric acid (150 ml), the resulting crystals were removed by filtration and the filtrate was washed with ether. The aqueous layer was concentrated and the residue was treated with ether to furnish which crystals which on recrystallization from ethanol/ether, gave 4'-(2''-ethoxycarbonylethyl)phenyl trans-4-guanidinomethylcyclohexanecarboxylate hydrochloride (17.9 g, 86.9%), m.p. 90°-91° C.

I.R.: $\nu_{max}$(cm$^{-1}$) 1725, 1740 (C=O)

Analysis: Found: C, 57.98, H, 7.10, N, 10.13, $C_{20}H_{29}N_3O_4$·HCl requires: C, 58.32, H, 7.34, n, 10.24.

EXAMPLE 4

Phenyltrans-4-guanidinomethylcyclohexanecarboxylate hydrochloride

A suspension of trans-4-guanidinomethylcyclohexanecarboxylic acid hydrochloride (11.8 g), phenol (5.6 g), and dicyclohexylcarbodiimide (12.4 g) in pyridine (75 ml) was stirred overnight at room temperature. After evaporation of solvent, the residue was treated with 0.1 N hydrochloric acid (200 ml), the insoluble materials removed by filtration and the filtrate was washed with ethylacetate. The aqueous layer was concentrated to 100 ml, the resulting crystals were filtered and washed with isopropylalcohol/isopropylether to give phenyl trans-4-guanidinomethylcyclohexanecarboxylate hydrochloride (12.5 g, 80.2%), m.p. 150°-153° C. This compound was recrystallized from methanol to give white crystal, phenyl trans-4-guanidinomethylcyclohexanecarboxylate hydrochloride, m.p. 159.5°-161.5° C.

I.R.: $\nu_{max}$(cm$^{-1}$) 1750 (C=O), 1620-1680 (C=N),

Analysis: Found: C, 57.49, H, 7.25, N, 13.27, $C_{15}H_{21}N_3O_2$·HCl requires: c, 57.78, H, 7.11, N, 13.48.

EXAMPLE 5

4'-(2''-Carboxyethyl)phenyl trans-4-guanidinomethylcyclohexanecarboxylate hydrochloride A suspension of trans-4-guanidinomethylcyclohexanecarboxylic acid hydrochloride (11.8 g), benzyl 4-hydroxyphenylpropionate (15.4 g) and dicyclohexylcarbodiimide (14.4 g) in pyridine (80 ml) was stirred overnight at room temperature. After evaporation of solvent, the residue was treated with a mixture of 0.1 N-hydrochloric acid (200 ml) and ethylacetate (100 ml), the insoluble materials were filtered off and the organic layer was separated. After evaporation to dryness methanol, acetic acid and water were added, then, the resulting clear solution was hydrogenated over 10% Pd/C. After absorption of theoretical amount of hydrogen, the catalyst was filtered off. The filtrate was concentrated to dryness, the crystals obtained were recrystallized from methanol/acetic acid to give the title compound (14.3 g, 74.5%), m.p. 295°-296° C.

I.R.: $\nu_{max}$(cm$^{-1}$) 1750(C=O), 1706(c=O), 1630-1680 (C=N)

Analysis: Found: C, 55.98, H, 6.51, N, 10.72. $C_{18}H_{25}N_3O_4$·HCl requires: C, 56.32, H, 6.83, N, 10.95.

EXAMPLE 6

2'-Benzyloxycarbonylphenyl trans-4-guanidinomethylcyclohexanecarboxylate hydrochloride A suspension of trans-4-guandinomethylcyclohexanecarboxylic acid hydrochloride (10.6 g), benzyl salicylate (11.4 g) and dicyclohexylcarbodiimide (11.3 g) in pyridine (100 ml) was stirred at 35°-40° C. for 15 hours. After removal of insoluble materials, the solvent was evaporated. The residue was treated with 0.1 N-hydrochloric acid (200 ml), the resulting crystals were obtained, and extracted with methanol. The extract was concentrated and water was added, the resulting solid was recrystallized from aqueous acetone to give 2'-benzyloxycarbonylphenyl trans-4-guanidinomethylcyclohexanecarboxylate hydrochloride (17.9 g, 89.2%), m.p. 70°-72.5° C.

I.R.: $\nu_{max}$(cm$^{-1}$) 1730 (C=O)

Analysis: Found: C, 61.38, H, 6.38, N, 9.19, $C_{23}H_{27}N_3O_4$·HCl requires: C, 61.95, H, 6.33, N, 9.42

The product obtained was recrystallized from methanol/ether to give a white crystal, 2'-benzyloxycarbonylphenyl trans-4-guanidinomethylcyclohexanecarboxylate hydrochloride, m.p. 83° C.

EXAMPLE 7

2'-Hydroxycarbonylphenyl trans-4-guanidinomethylcyclohexanecarboxylate hydrochloride A solution of 2'-benzyloxycarbonylphenyl trans-4-guanidinomethylcyclohexanecarboxylate hydrochloride (8.9 g) in acetic acid (30 ml) and methanol (10 ml) was hydrogenated over 10% Pd/C. After absorption of hydrogen (about 500 ml), the catalyst was filtered off. The filtrate was concentrated to dryness, the crystals were washed with ether, and recrystallized from ethanol/ether to give the title compound (6.5 g, 91.3%), m.p. 166°-168° C.

I.R.: $\nu_{max}$(cm$^{-1}$) 1750, 1690(C=O)

Analysis: Found: C, 53.85, H, 6.05, N, 11.42. $C_{16}H_{21}N_3O_4$·HCl requires: C, 54.01, H, 6.23, N, 11.81.

EXAMPLE 8

2'-Ethoxycarbonylphenyl trans-4-guanidinomethylcyclohexanecarboxylate hydrochloride A suspension of trans-4-guanidinomethylcyclohexanecarboxylic acid hydrochloride (7.1 g), ethyl salicylate (5.5 g) and dicyclohexylcarbodiimide (7.2 g) in pyridine (100 ml) was stirred at room temperature for 15 hours. After removal of insoluble materials by filtration the solution was concentrated. The residue was treated with 0.1 N-hydrochloric acid (100 ml), further insoluble materials were filtered off and the filtrate was washed with ether. After evaporation, the residue was treated with ether, and stirred, the resulting crude product was recrystallized from ethanol/ether to give 2'-ethoxycarbonylphenyl trans-4-guanidinomethylcyclohexanecarboxylate hydrochloride (8.4 g, 72.9%), m.p. 110°–111° C.

I.R.: $\nu_{max}$(cm$^{-1}$) 1740 (C=O)
Analysis: Found: C, 55.97, H, 6.72, N, 10.54. $C_{17}H_{25}N_3O_4$·HCl requires: C, 56.32, H, 6.83, N, 10.95.

EXAMPLE 9

2'-Methoxy-4'-formylphenyl trans-4-guanidinomethylcyclohexanecarboxylate hydrochloride A suspension of trans-4-guanidinomethylcyclohexanecarboxylic acid hydrochloride (7.1 g), vaniline (5.0 g) and dicyclohexylcarbodiimide (7.2 g) in pyridine (100 ml) was stirred at 30° C. for 15 hours. After removal of the insoluble materials the solution was concentrated. The residue was treated with a mixture of 0.1 N-hydrochloric acid (100 ml) and ethylacetate (100 ml), and stirred for 1 hour. Further insoluble materials were filtered off and the organic layer was separated. After evaporation to dryness, the residual solid was washed with ether and recrystallized from isopropyl alcohol/ether to give 2'-methoxy-4'-formylphenyl trans-4-guanidinomethylcyclohexanecarboxylate hydrochloride (9.6 g, 86.5%), m.p. 110°–111° C.

I.R.: $\nu_{max}$(cm$^{-1}$) 1760 (C=O)
Analysis: Found: C, 54.74, H, 6.66, N, 11.22. $C_{17}H_{23}N_3O_4$·HCl requires: C, 55.21, H, 6.54, N, 11.36.

EXAMPLE 10

2'-Phenoxycarbonylphenyl trans-4-guanidinomethylcyclohexanecarbodylate hydrochloride A suspension of trans-4-guanidinomethylcyclohexane carboxylic acid hydrochloride (27.5 g), phenylsalicylate (25.0 g) and dicyclohexylcarbodiimide (26.5 g) in dimethylformamide (100 ml) was stirred at room temperature for 21 hours. To this solution, water (150 ml) and concentrated hydrochloric acid (120 ml) were added, the resulting precipitated solid was washed with water. Then, the solid was treated with methanol, and the methanol layer was evaporated to dryness and solidified with ether to give 2'-phenoxycarbonylphenyl trans-4-guanidinomethylcyclohexanecarboxylate hydrochloride (34.1 g, 67.5%), m.p. 157°–162° C.

I.R.: $\nu_{max}$(cm$^{-1}$) 1740, 1750 (C=O)
NMR: $\delta CD_3OD$
0.7–3.1 (m, 12H)
6.8–8.1 (m, 9H)
Analysis: Found: C, 61.08, H, 5.95, N, 9.79. $C_{22}H_{25}N_3O_4$·HCl requires: C, 61.18, H, 6.07, N, 9.73.

EXAMPLE 11

3'-Benzyloxycarbonylphenyl trans-4-guanidinomethylcyclohexanecarboxylate hydrochloride 3'-Benzyloxycarbonylphenyl trans-4-guanidinomethylcyclohexanecarboxylic acid hydrochloride (109.8 g), benzyl 3-hydroxybenzoate (106.3 g) and dicyclohexylcarbodiimide (105.7 g) in pyridine (450 ml) was stirred at room temperature for 22 hours. After evaporation of pyridine, water (100 ml) was added and acidified with hydrochloric acid. The resulting slurry was treated by centrifugal separator. The solid obtained was treated with methanol, and the methanol layer was concentrated. Recrystallization of the residue from isopropylalcohol gave 3'-benzyloxycarbonylphenyl trans-4-guanidinomethylcyclohexanecarboxylate hydrochloride (169.5 g, 81.6%) m.p. 75°–80° C.

I.R.: $\nu_{max}$(cm$^{-1}$) 1725, 1755 (C=O)
NMR: $\delta CD_3OD$
0.8–3.2 (m, 12H)
5.3 (s, 2H)
6.9–8.0 (m, 9H)
Analysis: Found: C, 61.37, H, 6.18, N, 9.58. $C_{23}H_{27}N_3O_4$·HCl requires: C, 61.95, H, 6.33, N, 9.42.

EXAMPLE 12

3'-Hydroxycarbonyl trans-4-guanidinomethylcyclohexanecarboxylate hydrochloride

3'-Benzyloxycarbonylphenyl trans-4-guanidinomethylcyclohexanecarboxylate hydrochloride (80 g) was dissolved in a mixture of methanol (300 ml) and acetic acid (300 ml), and the solution was hydrogenated over 10% Pd/C. After absorption of theoretical amount of hydrogen, the catalyst was filtered off. The filtrate was concentrated to dryness, the crystals obtained were recrystallized from methanol to give the title compound (56.8 g, 89.0%), m.p. 197°–200° C.

I.R.: $\nu_{max}$(cm$^{-1}$) 1700, 1740 (C=O)
NMR: $\delta CD_3OD$
0.8–3.2 (m, 12H)
7.0–8.0 (m, 4H)
Analysis: Found: C, 53.96, H, 6.21, N, 11.89. $C_{16}H_{21}N_3O_4$·HCl requires: C, 54.01, H, 6.23, N, 11.81.

EXAMPLE 13

4'-Ethoxycarbonylphenyl trans-4-guanidinomethylcyclohexanecarboxylate hydrochloride A suspension of trans-4-guanidinomethylcyclohexanecarboxylic acid hydrochloride (35.4 g), ethyl 4-hydroxybenzoate (25 g) and dicyclohexylcarbodiimide (34.0 g) in pyridine (350 ml) was stirred at room temperature for 17 hours. After evaporation of pyridine, to the residue was added water (300 ml), and the mixture was acidified with hydrochloric acid. The resulting white solid was dissolved in methanol, and insoluble materials were filtered off. The methanol layer was concentrated and recrystallization of the residue from ethanol gave 4'-ethoxycarbonylphenyl trans-4-guanidinomethylcyclohexanecarboxylate hydrochloride (33.7 g, 58.5%), m.p. 181°–184° C.

I.R.: $\nu_{max}$(cm$^{-1}$) 1715, 1755 (C=O)
NMR: $\delta CD_3OD$
0.6–3.1 (m,t,15H)
4.3 (q,2H)
7.1, 8.0 (d,d,4H)
Analysis: Found: C, 56.21, H, 6.79, N, 11.03. $C_{18}H_{25}N_3O_4$·HCl requires: C, 56.32, H, 6.83, N, 10.95.

EXAMPLE 14

4'-Hydroxycarbonylphenyl trans-4-guanidinomethylcyclohexanecarboxylate hydrochloride By the procedure of Example 12, using 4'-benzyloxycarbonylphenyl trans-4-guanidinomethylcyclohexanecarboxylate hydrochloride (65 g) as starting material, 4'-hydroxycarbonylphenyl trans-4-guanidinomethylcyclohexanecarboxylate hydrochloride (45.8 g, 88.3%) was obtained. m.p. 225.5°–228.0° C.

I.R.: $\nu_{max}$(cm$^{-1}$) 1750(C=O)
NMR: $\delta$DMSO-d$_6$, D$_2$O
0.8–3.2 (m, 12H)
7.2, 8.0 (d,d, 4H)
Analysis: Found: C, 53.89, H, 6.21, N, 11.97. C$_{16}$H$_{21}$N$_3$O$_4$.HCl requires: C, 54.01, H, 6.23, N, 11.81.

EXAMPLE 15

3'-Methoxycarbonylphenyl trans-4-guanidinomethylcyclohexanecarboxylate hydrochloride A suspension of trans-4-guanidinomethylcyclohexanecarboxylic acid hydrochloride (35.4 g), methyl 3-hydroxybenzoate (22.8 g) and dicyclohexylcarbodiimide (34.0 g) in pyridine (300 ml) was stirred at room temperature for 24 hours. Following removal of insoluble materials and evaporation of pyridine, the residue was acidified with concentrated hydrochloric acid and extracted with chloroform. After concentration of chloroform layer, the residual solid was recrystallized from acetone to give 3'-methoxycarbonylphenyl trans-4-guanidinomethylcyclohexanecarboxylate hydrochloride (20.9 g, 37.7%), m.p. 138°–147° C.

I.R.: $\nu_{max}$(cm$^{-1}$) 1705, 1745(C=O)
NMR: $\delta$CD$_3$OD
0.8–3.2 (m, 12H)
3.9 (s, 3H)
7.0–8.1 (m, 12H)
Analysis: Found: C, 54.93, H, 6.48, N, 11.43. C$_{17}$H$_{23}$N$_3$O$_4$.HCl requires: C, 55.21, H, 6.51, N, 11.36.

EXAMPLE 16

3'-Pyridyl trans-4-guanidinomethylcyclohexanecarboxylate dihydrochloride

A suspension of trans-4-guanidinomethylcyclohexanecarboxylic acid hydrochloride (47.1 g), 3-hydroxypyridine (19.0 g) and dicyclohexylcarbodiimide (45.4 g) in pyridine (400 ml) was stirred at room temperature for 24 hours. The solid collected was extracted with methanol, and methanol layer was evaporated to dryness. The residue was recrystallized from methanol to give 3'-pyridyl trans-4-guanidinomethylcyclohexanecarboxylate dihydrochloride (36.1 g, 57.7%), m.p. 180°–185° C.

I.R.: $\nu_{max}$(cm$^{-1}$) 1750(C=O)
NMR: $\delta$CD$_3$OD
0.7–3.1 (m, 12H)
7.6–8.6 (m, 3H)
Analysis: Found: C, 47.98, H, 6.24, N, 16.31. C$_{14}$H$_{20}$N$_4$O$_2$.2HCl requires: C, 48.15, H, 6.35, N, 16.04.

EXAMPLE 17

β-Naphthyl trans-4-guanidinomethylcyclohexanecarboxylate hydrochloride

A suspension of trans-4-guanidinomethylcyclohexanecarboxylic acid hydrochloride (47.1 g), β-naphthol (28.8 g) and dicyclohexylcarbodiimide (45.4 g) in pyridine (400 ml) was stirred at room temperature for 24 hours. After evaporation of solvent, to the residue was added water (500 ml), and the mixture was acidified with hydrochloric acid. The resulting white crystals were dissolved in methanol (500 ml). After evaporation of methanol, the residue was recrystallized from methanol to give β-naphtyl trans-4-guanidinomethylcyclohexanecarboxylate hydrochloride (49.1 g, 67.8%), m.p. 195°–202° C.

I.R.: $\mu_{max}$(cm$^{-1}$) 1750(C=O)
NMR: $\delta$DMSO-d$_6$
0.8–3.1 (m, 12H)
6.9–8.2 (m, 7H)
Analysis: Found: C, 62.52, H, 6.59, N, 11.89. C$_{19}$H$_{23}$N$_3$O$_2$.HCl requires: C, 63.06, H, 6.68, N, 11.61.

EXAMPLE 18

α-Naphthyl trans-4-guanidinomethylcyclohexanecarboxylate hydrochloride

By the procedure of Example 17, using α-naphthol (28.8 g) instead of β-naphthol as starting material, α-naphthyl trans-4-guanidinomethylcyclohexanecarboxylate hydrochloride (36.9 g, 51.0%) was obtained. m.p. 191°–203° C.

I.R.: $\nu_{max}$(cm$^{-1}$) 1745 (C=O)
NMR: $\delta$CD$_3$OD
0.9–3.0 (m, 12H)
7.2–8.1 (m, 7H)
Analysis: Found: C, 62.71, H, 6.62, N, 11.83. C$_{19}$H$_{23}$N$_3$O$_2$.HCl requires: C, 63.06, H, 6.68, N, 11.61.

EXAMPLE 19

2'-Formylphenyl trans-4-guanidinomethylcyclohexanecarboxylate hydrochloride

A suspension of trans-4-guanidinomethylcyclohexanecarboxylic acid hydrochloride (94.3 g), salicyl aldehyde (50 g) and dicyclohexylcarbodiimide (90.8 g) in pyridine (600 ml) was stirred at room temperature for 16 hours. After evaporation of pyridine, to the residue was added water (200 ml), the mixture was acidified with hydrochloric acid. The resulting white solid was filtered and extracted with methanol (500 ml). The insoluble matter was removed by filtration and the filtrate was concentrated. To the residue was added acetone (200 ml), insoluble materials were removed by filtration. The filtrate was concentrated. The residue was crystallized from water to give 2'-formylphenyl trans-4-guanidinomethylcyclohexanecarboxylate hydrochloride (53.2 g, 39.1%), m.p. 135°–138° C.

I.R.: $\nu_{max}$(cm$^{-1}$) 1740(C=O)
NMR: $\delta$CD$_3$OD
0.8–3.2 (m, 12H)
5.4 (s, 1H)
6.8 (m, 4H)
Analysis: Found: C, 55.98, H, 6.31, N, 12.63. C$_{16}$H$_{21}$N$_3$O$_3$.HCl requires: C, 56.55, H, 6.53, N, 12.37.

0.1 mM of this compound inhibited 56% hydrolytic activity by urokinase.

EXAMPLE 20

2'-Methoxyphenyl trans-4-guanidinomethylcyclohexanecarboxylate hydrochloride

A suspension of trans-4-guanidinomethylcyclohexanecarboxylic acid hydrochloride (47.1 g), o-methoxyphenol (24.8 g) and dicyclohexylcarbodiimide (45.4 g) was stirred at room temperature for 24 hours. After removal of insoluble materials, the solution was concentrated to dryness. To the residue was added water (300 ml), the solution was acidified with hydrochloric acid. The resulting crystals were filtered and recrystallized from isopropylalcohol to give the title compound (57.5 g, 84.1%), m.p. 141°–145° C.

I.R.: $\nu_{max}$(cm$^{-1}$) 1760(C=O)
NMR: $\delta$CD$_3$OD
0.7–3.0 (m, 12H)
3.8 (s, 3H)
6.8–7.3 (m, 4H)
Analysis: Found: C, 56.18, H, 7.01, N, 12.31. $C_{16}H_{26}N_3O_3 \cdot HCl$ requires: C, 56.22, H, 7.08, N, 12.29.

0.1 mM of this compound inhibited 50% hydrolytic activity by urokinase.

EXAMPLE 21

4'-Methoxyphenyl trans-4-guanidinomethylcyclohexanecarboxylate hydrochloride

A suspension of trans-4-guanidinomethylcyclohexanecarboxylic acid hydrochloride (47 g), p-methoxyphenol (25 g) and dicyclohexylcarbodiimide (45 g) in dimethylformamide (200 ml) was stirred at room temperature for 23 hours. To the reaction mixture were added water (200 ml), ice (100 g) and concentrated hydrochloric acid (200 ml). The resulting crystals were filtered and washed with water, and dissolved in methanol (300 ml). The insoluble materials were filtered off and the filtrate was concentrated to dryness. The residue was crystallized from methanol to give the title compound (29.2 g, 42.4%). m.p. 203°–205° C.

I.R.: $\nu_{max}$(cm$^{-1}$) 1745(C=O)
NMR: $\delta$CD$_3$OD
0.7–3.1 (m, 12H)
3.8 (s, 3H)
7.0 (s, 4H)
Analysis: Found: C, 56.19, H, 7.01, N, 12.35. $C_{16}H_{23}N_3O_2 \cdot HCl$ requires: C, 56.22, H, 7.08, N, 12.29.

0.1 mM of this compound inhibited 52% hydrolytic activity by urokinase.

EXAMPLE 22

2'-Ethoxyphenyl trans-4-guanidinomethylcyclohexanecarboxylate hydrochloride

A suspension of trans-4-guanidinomethylcyclohexanecarboxylic acid hydrochloride (70.7 g), o-ethoxyphenol (41.5 g) and dicyclohexylcarbodiimide (68.1 g) in dimethylformamide (300 ml) was stirred at room temperature for 24 hours. To the reaction mixture were added water (100 ml) and concentrated hydrochloric acid (350 ml). The resulting crystals were filtered and washed with water, dissolved in methanol (300 ml). The insoluble materials were filtered off and the filtrate was concentrated to dryness. The residue was dissolved in acetone and treated with ether to give the title compound (65.0 g, 60.9%), m.p. 144°–148° C.

I.R.: $\nu_{max}$(cm$^{-1}$) 1750(C=O)
NMR: $\delta$CD$_3$OD
0.7–3.0 (m, t, 15H)
4.0 (1, 2H)
6.7–7.2 (m, 4H)
Analysis: Found: C, 56.94, H, 7.01, N, 12.11. $C_{17}H_{25}N_3O_3 \cdot HCl$ requires: C, 56.38, H, 7.36, N, 11.81.

EXAMPLE 23

2'-Acetylphenyl trans-4-guanidomethycylohexanecarboxylate hydrochloride

A suspension of trans-4-guanidinomethylcyclohexanecarboxylic acid hydrochloride (34.7 g), o-hydroxyacetophenone (20.0 g) and dicyclohexylcarbodiimide (33.3 g) in pyridine (300 ml) was stirred at room temperature for 24 hours. After removal of insoluble materials, the solution was concentrated to dryness. To the residue was added water (200 ml) and the mixture was acidified with hydrochloric acid, then extracted with chloroform. The chloroform layer was concentrated to dryness, and the residue was recrystallized from isopropylalcohol to give the title compound (22.7 g, 43.7%), m.p. 159°–166° C.

I.R.: $\nu_{max}$(cm$^{-1}$) 1750(C=O)
NMR: $\delta$CD$_3$OD
0.8–3.1 (m,s, 15H)
6.9–8.0 (m, 4H)
Analysis: Found: C, 57.47, H, 6.78, N, 12.03. $C_{17}H_{23}N_3O_3 \cdot HCl$ requires: C, 57.70, H, 6.84, N, 11.88.

0.05 mM of this compound inhibited 50% hydrolytic activity by chymotrypsi.

EXAMPLE 24

4'-Acetylphenyl trans-4-guanidinomethylcyclohexanecarboxylate hydrochloride

A suspension of trans-4-guanidinomethylcyclohexanecarboxylic acid hydrochloride (35.4 g), p-hydroxyacetophenone (20.4 g) and dicyclohexylcarbodiimide (34.0 g) in pyridine (300 ml) was stirred at room temperature for 24 hours. After removal of insoluble materials, the solution was concentrated to dryness. To the residue was added water (300 ml) and the mixture was acidified with hydrochloric acid. The resulting crystals were filtered and recrystallized from ethanol to give the title compound (42.4 g, 80%), m.p. 175°–180° C.

I.R.: $\nu_{max}$(cm$^{-1}$) 1750(C=O)
NMR: $\delta$CD$_3$OD
0.7–3.1 (m,s, 15H)
7.2, 8.0 (d,d, 4H)
Analysis: Found: C, 57.63, H, 6.81, N, 11.92. $C_{17}H_{23}N_3O_3 \cdot HCl$ requires: C, 57.70, H, 6.84, N, 11.88.

EXAMPLE 25

2'-Phenylphenyl trans-4-guanidinomethylcyclohexanecarboxylate hydrochloride

A suspension of trans-4-guanidinomethylcyclohexanecarboxylic acid hydrochloride (35.4 g), o-phenylphenol (25.5 g) dicyclohexylcarbodiimide (34.0 g) in pyridine (300 ml) was stirred at room temperature for 24 hours. The solution was concentrated to dryness. To the residue was added water (300 ml), and the solution was acidified with hydrochloric acid, then extracted with chloroform. The chloroform layer was washed with water and evaporated to give the title compound (55.5 g, 94.6%), m.p. 78°–85° C.

I.R.: $\nu_{max}$(cm$^{-1}$) 1750(C=O)
NMR: $\delta$CD$_3$OD
0.7–3.0 (m, 12H)
6.8–7.5 (m, 9H)
Analysis: Found: C, 64.69, H, 6.49, N, 11.04. C$_{21}$H$_{25}$N$_3$O$_2$.HCl requires: C, 65.02, H, 6.76, N, 10.83.

EXAMPLE 26

4′-Phenylphenyl trans-4-guanidinomethylcyclohexanecarboxylate hydrochloride

A suspension of trans-4-guanidinomethylcyclohexanecarboxylic acid hydrochloride (47.1 g), p-phenylphenol (34.0 g) and dicyclohexylcarbodiimide (44.5 g) in dimethylformamide (250 ml) was stirred at room temperature for 24 hours. After removal of insoluble materials, the solution was evaporated to dryness. To the residue was added water (300 ml), and the solution was acidified with hydrochloric acid. The resulting crystals obtained were recrystallized from methanol to give the title compound (47.9 g, 61.7%)., m.p. 185°–196° C.

I.R.: $\nu_{max}$(cm$^{-1}$) 1750(C=O)
NMR: $\delta$CD$_3$OD
0.8–3.1 (m, 12H)
6.9–7.8 (m, 9H)
Analysis: Found: C, 64.94, H, 6.57, N, 11.03. C$_{21}$H$_{25}$N$_3$O$_3$.HCl requires: C, 65.02, H, 6.76, N, 10.83.

EXAMPLE 27

4′-Phenoxycarbonylphenyl trans-4-guanidinomethylcyclohexanecarboxylate hydrochloride A suspension of trans-4-guanidinomethylcyclohexanecarboxylic acid hydrochloride (22.0 g), phenyl 4-hydroxybenzoate (20.0 g) and dicyclohexylcarbodiimide (22.9 g) in pyridine (100 ml) was stirred at room temperature for 30 hours. After evaporation of pyridine, to the residue was added water (300 ml), and the solution was acidified with hydrochloric acid. The resulting solid obtained was extracted with methanol (500 ml). After concentration of the extract, the residue was recrystallized from ethanol to give 4′-phenoxycarbonylphenyl trans-4-guanidinomethylcyclohexanecarboxylate hydrochloride (21.5 g, 53.5%), m.p. 166°–170° C.

I.R.: $\nu_{max}$(cm$^{-1}$) 1740, 1745 (C=O)
NMR: $\delta$CD$_3$OD
0.7–3.1 (m, 12H)
7.0–8.3 (m, 9H)
Analysis: Found: C, 61.09, H, 6.12, N, 9.78. C$_{22}$H$_{25}$N$_3$O$_4$.HCl requires: C, 61.18, H, 6.07, N, 9.73.

EXAMPLE 28

3′-Anisyloxycarbonylphenyl trans-4-guanidinomethylcyclohexanecarboxylate hydrochloride A suspension of 3′-carboxyphenyl trans-4-guanidinomethylcyclohexanecarboxylate hydrochloride (7.12 g), p-anisalcohol (2.76 g) and dicyclohexylcarbodiimide (5.16 g) in pyridine (30 ml) was stirred at room temperature for 18 hours. To this reaction mixture was added water (100 ml) and the solution was acidified with hydrochloric acid and stirred for 1 hour. The resulting solid obtained was extracted with methanol (50 ml). After evaporation of the methanol, the residue was recrystallized from aqueous methanol to give 3′-anisyloxycarbonylphenyl trans-4-guanidinomethylcyclohexanecarboxylate hydrochloride (8.4 g, 88.2%), m.p. 90°–93° C.

I.R.: $\nu_{max}$(cm$^{-1}$) 1725, 1755(C=O)
NMR: $\delta$CD$_3$OD
0.8–3.2 (s, 12H)
3.8 (s, 3H)
5.3 (s, 2H)
6.9–8.0 (m, 8H)
Analysis: Found: C, 60.35, H, 6.31, N, 8.89. C$_{24}$H$_{29}$N$_3$O$_5$.HCl requires: C, 60.56, H, 6.35, N, 8.83

EXAMPLE 29

3′-Hydroxycarbonylphenyl trans-4-guanidinomethylcyclohexanecarboxylate hydrochloride By the procedure of Example 12, using 3′-anisyloxycarbonylphenyl trans-4-guanidinomethylcyclohexanecarboxylate hydrochloride (2.5 g) as the starting material, the title compound (1.5 g, 80,3%) was obtained.

EXAMPLE 30

4′-Benzyloxycarbonylphenyl trans-4-guanidinomethylcyclohexanecarboxylate hydrochloride A suspension of trans-4-guanidinomethylcyclohexanecarboxylic acid hydrochloride (119.4 g), benzyl 4-hydroxybenzoate (115.6 g) and dicyclohexylcarbodiimide (114.9 g) in dimethylformamide (430 ml) was stirred at room temperature for 20 hours. To this reaction mixture was added water (1500 ml), and the solution was acidified with hydrochloric acid (500 ml). The resulting solid obtained was extracted with methanol (500 ml). After removal of insoluble materials by filtration, the filtrate was concentrated and the residue was recrystallized from methanol/water to give 4′-benzyloxycarbonylphenyl trans-4-guanidinomethylcyclohexanecarboxylate hydrochloride (148.5 g, 65.8%), m.p. 134°–138° C.

I.R.: $\nu_{max}$(cm$^{-1}$) 1710, 1750(C—O)
NMR: $\delta$CD$_3$OD
0.8–3.2 (m, 12H)
5.35 (s, 2H)
7.2, 8.1 (d,d, 4H)
7.4 (s, 5H)
Analysis: Found: C, 61.47, H, 6.18, N, 9.53. C$_{23}$H$_{27}$N$_3$O$_4$.HCl requires: C, 61.95, H, 6.33, N, 9.42.

EXAMPLE 31

4′-Benzyloxycarbonylphenyl trans-4-guanidinomethylcyclohexanecarboxylate hydrochloride A suspension of 4′-hydroxycarbonyphenyl trans-4-guanidinomethylcyclohexanecarboxylate hydrochloride (2.15 g), benzylalcohol (0.65 g) and 1-ethyl-3-(3′-dimethylaminopropyl)carbodiimide hydrochloride (1.39 g) in pyridine (10 ml) was stirred at room temperature for 30 hours. To this reaction mixture was added water (50 ml), and the solution was acidified with hydrochloric acid, the resulting crystals were filtered and recrystallized from methanol/water to give the title compound (1.48 g, 55.3%).

EXAMPLE 32

2'-Benzyloxycarbonylphenyl trans-4-guanidinomethylcyclohexanecarboxylate hydrochloride A suspension of trans-4-guanidinomethylcyclohexanecarboxylic acid hydrochloride (5.89 g), benzyl salicylate (5.71 g) and 1-ethyl-3-(3'-dimethylaminopropyl)-carbodiimide hydrochloride (5.75 g) in pyridine (25 ml) was stirred at room temperature for 24 hours. To this reaction mixture was added water (50 ml), and the solution was acidified with hydrochloric acid. The resulting solid was filtered and washed with water, and recrystallized from methanol/ether to give the title compound (9.27 g, 83.2%).

EXAMPLE 33

3'-Methoxyphenyl trans-4-guanidinomethylcyclohexanecarboxylate hydrochloride A suspension of trans-4-guanidinomethylcyclohexanecarboxylic acid hydrochloride (35.4 g), m-methoxyphenol (18.6 g) and dicyclohexylcarbodiimide (34.0 g) in pyridine (300 ml) was stirred at room temperature for 24 hours. After removal of insoluble materials, the residue was acidified with hydrochloric acid and extracted with chloroform. Following concentration of chloroform layer under reduced pressure, the residue was washed with water. The resulting solid was filtered and recrystallized from ethanol to give the title compound (28.4 g, 55.4%), m.p. 125.5°–131.5° C.

I.R.: $\nu_{max}$(cm$^{-1}$) 1740(C=O)
NMR: $\delta$CD$_3$OD
1.0–3.1 (m, 12H)
3.8 (s, 3H)
6.6–7.45 (m, 4H)

EXAMPLE 34

4'-Formylphenyl trans-4-guanidinomethylcyclohexanecarboxylate hydrochloride

A suspension of trans-4-guanidinomethylcyclohexanecarboxylic acid hydrochloride (35.4 g), p-hydroxybenzaldehyde (18.3 g) and dicyclohexylcarbodiimide (34.0 g) in pyridine (300 ml) was stirred at room temperature for 24 hours. After evaporation of pyridine, to the residue was added water (100 ml), and the solution was acidified with hydrochloric acid. The resulting solid was filtered and extracted with methanol. The extract was concentrated to dryness and the residue was recrystallized from methanol to give the title compound (22.5 g, 44.2%), m.p. 157.5°–163.5° C.

I.R.: $\nu_{max}$(cm$^{-1}$) 1750(C=O)
NMR: $\delta$CD$_3$OD
0.9–3.1 (m, 12H)
7.25, 7.95 (d,d, 4H)

EXAMPLE 35

4'-Propionylphenyl trans-4-guanidinomethylcyclohexanecarboxylate hydrochloride A suspension of trans-4-guanidinomethylcyclohexanecarboxylic acid hydrochloride (35.4 g), p-hydroxypropiophenon (22.5 g) and dicyclohexylcarbodiimide (34.0 g) in pyridine (300 ml) was stirred at room temperature for 24 hours. The resulting crystals were filtered and extracted with methanol (500 ml). The extract was evaporated to dryness and the residue was recrystallized from methanol to give the title compound (39.6 g, 71.8%), m.p. 179°–185° C.

I.R.: $\nu_{max}$(cm$^{-1}$) 1750(C=O)
NMR: $\delta$CD$_3$OD
0.9–3.0 (m, 17H)
7.1, 7.95 (d,d, 4H)

EXAMPLE 36

4'-Diphenyl trans-4-guanidinomethylcyclohexanecarboxylate methanesulfonate

By the procedure of Example 26, using trans-4-guanidinomethylcyclohexanecarboxylic acid methanesulfonate(2.95 g) instead of trans-4-guanidinomethylcyclohexanecarboxylic acid hydrochloride, the title compound(3.2 g, 71.4%) was obtained. m.p. 207°–210° C.

EXAMPLE 37

2'-Benzyloxycarbonylphenyl trans-4-guanidinomethylcyclohexanecarboxylate p-toluenesulfonate By the procedure of Example 6, using trans-4-guanidinomethylcyclohexanecarboxylic acid p-toluenesulfonate(3.71 g) instead of trans-4-guanidinomethylcyclohexanecarboxylic acid hydrochloride, the title compound(4.3 g, 73.9%) was obtained. m.p. 110°–114° C.

I.R.: 84 $_{max}$(cm$^{-1}$) 1735, 1760(C=O)
NMR: $\delta$CD$_3$OD
0.7–3.0 (m,s, 15H)
5.3 (s, 2H)
7.0–8.1 (m, 13H)

EXAMPLE 38

$\beta$-Naphthyl trans-4-guanidinomethylcyclohexanecarboxylate hydrochloride A suspension of trans-4-guanidinomethylcyclohexanecarboxylic acid hydrochloride(1.8 g), $\beta$-naphtol(1.44 g), sulfuric acid(0.05 g) and boric acid(0.03 g) in a mixture of dimethylsulfoxide(10 ml) and xylene(50 ml) was heated under reflux conditions for 20 hours. The resulting water was removed by azeotropy with xylene. Following concentration of the reaction mixture, the residue was chromatographed on a column of silica gel with chloroform/methanol as eluent to give the title compound.

EXAMPLE 39

4'-Diphenyl trans-4-guanidinomethylcyclohexanecarboxylate hydrochloride

A mixture of trans-4-guanidinomethylcyclohexanecarboxylic acid hydrochloride(23.6 g), 4-hydroxybiphenyl(17.0 g) and phosphorousoxychloride(7.7 g) was stirred at 80°–85° C. for 2 hours. After adding of toluene(50 ml), the mixture was stirred at 80°–85° C. for further 2 hours. The solvent was removed by decantation and water was added. The solution was set aside overnight in a refrigerator, the resulting white crystals were recrystallized from methanol to give the title compound(12.8 g, 61.3%).

EXAMPLE 40

4'-(2''-Benzyloxycarbonylethyl)phenyl trans-4-guanidinomethylcyclohexanecarboxylate hydrochloride:

A suspension of 4'-(2''-carboxyethyl)phenyl trans-4-guanidinomethylcyclohexanecaboxylate hydrochloride(1.92 g) in thionylchloride (10 ml) was stirred at 60° C. for 1 hour. Following evaporation of excess thionylchloride, the residue was dissolved in chloroform (15 ml). The resulting pale yellow solution was added at room temperature to a solution of benzylalcohol(0.65 g) and triethylamine(0.51 g) in chloroform(5 ml). After stirring at 35°–40° C. for 5 hours, the solvent was evaporated and the residue was solidified with water to give the title compound(1.4 g, 59.1%).

EXAMPLE 41

4'-(2''-Benzyloxycarbonylethyl)phenyl trans-4-guanidinomethylcyclohexanecarboxylate hydrochloride A suspension of 4'-(2''-carboxyethyl)phenyl trans-4-guanidinomethylcyclohexanecarboxylate hydrochloride(1.92 g) and benzyl alcohol (5 ml) was stirred at 130°–135° C. for 10 hours. After evaporation of excess benzyl alcohol, the residue was recrystallized from methanol/ether to give the title compound(1.2 g, 50.6%).

EXAMPLE 42

3'-Methoxycarbonylphenyl trans-4-guanidinomethylcyclohexanecarboxylate hydrochloride A suspension of 3'-carboxyphenyl trans-4-guanidinomethylcyclohexanecarboxylate hydrochloride(3.56 g) in thionyl chloride(10 ml) was refluxed for 30 minutes. Following concentration of the reaction mixture, the residue was dissolved in chloroform(10 ml), and to the solution was added methanol(5 ml) under cooling. After stirring for 30 minutes, the solution was set aside overnight in a refrigerator. The resulting crystals were filtered and washed with a mixture of water and acetone to give the title compound(2.5 g, 67.6%).

EXAMPLE 43

2'-Benzyloxycarbonylphenyl trans-4-guanidinomethylcyclohexanecarboxylate hydrochloride monohydrate 2'-Benzyloxycarbonylphenyl trans-4-guanidinomethylcyclohexanecarboxylate hydrochloride was recrystallized from acetone/water(85/15), and dried at 40° C. to give the title compound. m.p. 96°–150° C.
NMR: δpyridine-d
1.0–3.4 (m, 12H)
5.25 (s, 2H)
5.4 (s, 2H)
7.3–9.1 (m, 14H)
Analysis: Found: C, 59.61, H, 6.57, N, 9.18, Cl, 7.67
$C_{23}H_{27}N_3O_4 \cdot HCl \ H_2O$ requires: C, 59.54, H, 6.52, N, 9.06, Cl, 7.64.
Water Determination(Karl Fischer): Found: 3.98
$C_{23}H_{27}N_3O_4 \cdot HCl \ H_2O$ requires: 3.88.

EXAMPLE 44

4'-Ethoxycarbonylmethylcarbonylphenyl trans-4-guanidinomethylcyclohexanecarboxylate hydrochloride A solution of trans-4-guanidinomethylcyclohexanecarboxylic acid hydrochloride (9.4 g), ethoxycarbonylmethyl-p-hydroxybenzoate (9.0 g) and dicyclohexylcarbodiimide (9.1 g) in dimethylformamide (50 ml) was stirred at room temperature for 24 hours. Insoluble materials were removed by filtration, and the filtrate was evaporated to dryness. To the residue was added water, and the solution was acidified with hydrochloric acid and extracted with chloroform. The extract was evaporated to dryness. The residue was recrystallized from methanol to obtain the title compound (10.6 g, 60%).
m.p.: 140°–145° C.
I.R.: $\nu_{max}(cm^{-1})$ 1735, 1745, 1760 (C=O)
NMR: δCD$_3$OD
0.9–3.1 (m,t, 15H)
4.25 (q, 2H)
4.9 (s, 2H)
7.25, 8.1 (d,d, 4H)

EXAMPLE 45

4'-Diphenyl trans-4-guanidinomethylcyclohexanecarboxylate hydrochloride

A solution of trans-4-guanidinomethylcyclohexanecarboxylic acid methanesulfonate (1.0 g) and dimethylformamide (0.5 ml) in thionyl chloride (5 ml) was heated at 55°–60° C. for 2.5 hours. After being cooled, the reaction mixture was washed with petroleum ether and dissolved in chloroform. The resulting clear solution was added to a solution of p-phenyl-phenol (0.69 g) in pyridine (5 ml), and the mixture was stirred overnight at room temperature. The reaction mixture was evaporated, and to the residue was added water. The solution was extracted with chloroform. The extract was concentrated and chromatographed on a column filled with silica gel using chloroform/methanol as an eluent. The resulting crude product was then treated with ether/methanol/6 N hydrochloric acid to give the title compound.

EXAMPLE 46

4-Diphenyl trans-4-guanidinomethylcyclohexanecarboxylate hydrochloride

A mixture of trans-4-guanidinomethylcyclohexanecarboxylic acid hydrochloride (1.0 g) and thionyl chloride (5 ml) was refluxed for 2 hours. After concentration, to the reaction mixture was added chloroform (10 ml). The solution thus obtained was added to a solution of p-phenylphenol (0.7 g) in pyridine (5 ml) and heated at 40°–50° C. for 2 hours. To the reaction mixture was added hydrochloric acid, and the resulting solution was agitated and purified chromatographically to obtain the title compound.

EXAMPLE 47

4'-Carboxymethylphenyl trans-4-guanidinomethylcyclohexanecarboxylate hydrochloride A suspension of trans-4-guanidinomethylcyclohexanecarboxylic acid hydrochloride (10.64 g), benzyl p-hydroxyphenylacetate (10.94 g) and dicyclohexylcarboxylicimide (11.18 g) in pyridine (40 ml) was stirred at room temperature for 40 hours. After removal of insoluble materials by filtration, the filtrate was concentrated, and to the residue was added water. The solution was acidified with hydrochloric acid to obtain precipitated materials, which precipitates were collected by filtration and extracted with methanol. The extract obtained was evaporated to dryness in vacuo. The oily residue was dissolved in methanol acetic acid and hydrogenated over pd-c. After absorption of hydrogen, the catalyst was removed by filtration, and the filtrate was concentrated. To the residue was added acetone to obtain crystals. The crystals were collected by filtration and recrystallized from ethanol to give the title compound (5.4 g, 32.4%). m.p.: 174°–176.5° C.

I.R.: $\nu_{max}(cm^{-1})$ 1720, 1750 (C=O)
NMR: $\delta CD_3OD$
0.9–3.1 (m, 12H)
3.6 (3, 2H)
6.95–7.4 (m, 4H)

EXAMPLE 48

4'-(2''-Benzyloxycarbonyl)phenyl trans-4-guanidinomethylcyclohexancarboxylate hydrochloride Ethylchloroformate (0.65 g) was added to a suspension of 4'-(2''-carboxyethyl)phenyl trans-4-guanidinomethylcyclohexanecarboxylate hydrochloride (1.92 g) in pyridine (3 ml) and chloroform (10 ml) at −15° to −10° C. After agitation of the mixture at the same temperature for 1 hour, to the reaction mixture was added benzyl alcohol (1.08 g). The resulting solution was stirred continuously for 30 minutes at −15° to −10° C. The reaction mixture was evaporated to dryness in vacuo, and to the residue were water and hydrochloric acid. The solution thus obtained was extracted with chloroform. The solvent was removed from the extract. To the residue was added water to give the title compound.

EXAMPLE 49

4'-Carboxymethylphenyl trans-4-guanidinomethylcyclohexanecarboxylate hydrochloride (1) A solution of trans-4-guanidinomethylcyclohexanecarboxylic acid hydrochloride (4.7 g), tert-butyl p-hydroxyphenyl acetate (5.5 g) and dicyclohexylcarbodiimide (6.2 g) in dimethylformamide (20 ml) was stirred at room temperature for 20 hours. The reaction mixture was evaporated in vacuo, and to the residue was added chloroform. Insoluble materials were removed by filtration, and the filtrate was washed with water. The thus obtained chloroform layer was concentrated to give 4'-tert-butoxycarbonylmethylphenyl trans-4-guanidinomethylcyclohexanecarboxylate hydrochloride (6.9 g, 81.0%). m.p.: 110°–125° C.

(2) A solution of 4'-tert-butoxycarbonylmethylphenyl trans-4-guanidinomethylcyclohexanecarboxylate hydrochloride (3.0 g) in acetic acid (30 ml) and a 15% hydrogen chloride-acetic acid solution was stirred at room temperature for 4 hours. The reaction mixture was evaporated to dryness in vacuo to give the title compound.

EXAMPLE 50

2'-Benzyloxycarbonylphenyl trans-4-guanidinomethylcyclohexanecarboxylate hydrochloride (1) trans-4-Guanidinomethylcyclohexanecarboxylic acid chloride hydrochloride:

A suspension of trans-4-guanidinomethylcyclohexanecarboxylic acid hydrochloride (1.2 g) and thionyl chloride (15 ml) was stirred at room temperature for 3 hours. Thereafter, excess thionyl chloride was removed by distillation under reduced pressure. The residue was washed with anhydrous ethyl ether to obtain trans-4-guanidinomethylcyclohexanecarboxylic acid chloride hydrochloride (1.2 g) as colorless powder.

IR $_{max}{}^{nujol}$ cm$^{-1}$: 1790 (C=O)

(2) 2'-Benzyloxycarbonylphenyl trans-4-guanidinomethylcyclohexanecarboxylate hydrochloride:

A solution of triethylamine (0.75 g) in anhydrous methylenechloride (2 ml) was added to a suspension of trans-4-guanidinomethylcyclohexanecarboxylic acid chloride hydrochloride (1.2 g) and benzyl salicylate (1 g) in anhydrous methylenechloride (10 ml) at 0° C., and the resulting mixture was stirred at 0° C. for 10 hours. After distillation of the solvent, the residue was washed with a saturated sodium hydrogen carbonate solution to remove unreacted trans-4-guanidinomethylcyclohexanecarboxylic acid, and to the resulting residue was added anhydrous sodium sulfate. Then, the mixture was extracted with methylene chloride. After distillation of the solvent, the residue was washed with ether to remove unreacted benzyl salicylate. To the residue was added isopropyl alcohol, and insoluble materials were then removed by filtration. The solvent was removed from the filtrate by distillation, and the resulting residue was recrystallized from water to give 2'-benzyloxycarbonylphenyl trans-4-guanidinomethylcyclohexanecarboxylate hydrochloride monohydrate (320 mg) as colorless crystals.

EXAMPLE 51

2'-Benzyloxycarbonylphenyl trans-4-guanidinomethylcyclohexanecarboxylate hydrochloride monohydrate trans-4-Guanidinomethylcyclohexanecarboxylic acid hydrochloride (1.72 g) and triethylamine (0.74 g) were suspended in methylenechloride (20 ml), and to the suspension was added isobutyloxycarbonylchloride (1 g) at −5° C. To the resulting mixture, which had been stirred at −5° C. for 30 minutes, was added benzyl salicylate (1.66 g). The resulting mixture was stirred for 2 hours under ice cooling and further stirred for 36 hours at room temperature. After distillation of the solvent, the residue was washed with a saturated sodium hydrogencarbonate solution and extracted with methylenechloride. After distillation of the solvent, the residue was washed with ether and purified by thin-layer chromatography (n-butanol:acetic acid:water=4:1:1) to give 2'-benzyloxycarbonylphenyl trans-4-guanidinomethylcyclohexanecarboxylate hydrochloride monohydrate (285 mg).

EXAMPLE 52

Tablets: These contain the following materials in 220 mg of a film-coating tablet.

| | |
|---|---|
| Compound 1 | 50 mg |
| Cornstarch | 100 mg |
| Crystalline cellose | 50 mg |
| Magnesium stearate | 1 mg |
| Hydroxypropyl methyl cellose | 15 mg |
| Hydroxypropyl cellose | 4 mg |
| Total | 220 mg |

Compound 1 is the same as defined above.

Granules: These contain the following materials in 1000 mg of granules.

| | |
|---|---|
| Compound 1 | 100 mg |
| Avicel | 500 mg |
| Cornstarch | 400 mg |
| Total | 1000 mg |

Compound 1 is the same as defined above.

Having fully described the invention, it will be apparent to one skilled in this art that many changes and modifications can be made without departing from the spirit or scope of the invention.

Accordingly, what is intended to be covered and claimed by Letters Patent of the United States is:

1. A compound of the formula:

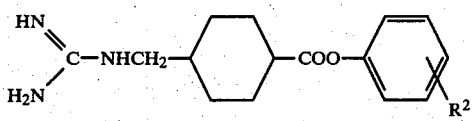

wherein $R_2$ represents a hydrogen atom, a lower alkoxy, formyl, lower alkanoyl, phenyl group, or a group of the formula, $—(CH_2)_nCOOR_3$, wherein $R_3$ represents a hydrogen atom, or a lower alkyl, phenyl, benzyl, anisyl or lower alkoxycarbonylmethyl group, and n represents an integer of 0 to 2, or a pharmaceutically acceptable salt thereof.

2. A compound of the formula:

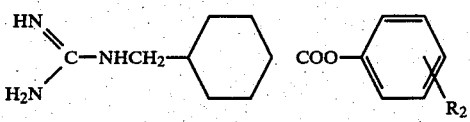

wherein $R_2$ represents a hydrogen atom, a lower alkoxy, formyl, lower alkanoyl, phenyl group, or a group of the formula $—(CH_2)_nCOOR_3$, wherein $R_3$ represents a hydrogen atom, or a lower alkyl, phenyl, benzyl, anisyl or lower alkoxycarbonylmethyl group, and n represents an integer of 0 to 2, or a pharmaceutically acceptable salt thereof.

3. A compound of the formula:

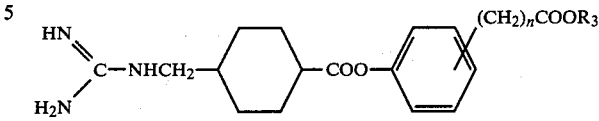

wherein $R_3$ represents a hydrogen atom, or a lower alkyl, phenyl, benzyl, anisyl or lower alkoxycarbonylmethyl group, and n represents an integer 0 to 2, or a pharmaceutically acceptable salt thereof.

4. (2'-Benzyloxycarbonyl)phenyl trans-4-guanidinomethylcyclohexanecarboxylate hydrochloride.

5. (2'-Benzyloxycarbonyl)phenyl trans-4-guanidinomethylcyclohexanecarboxylate hydrochloride monohydrate.

6. (2'-Anisyloxycarbonyl)phenyl trans-4-guanidinomethylcyclohexanecarboxylate hydrochloride.

7. (2'-Carboxyl)phenyl trans-4-guanidinomethylcyclohexanecarboxylate hydrochloride.

8. An anti-ulcer agent comprising a compound of the formula:

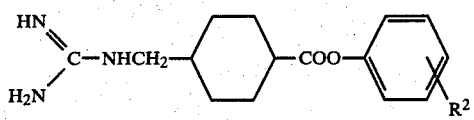

wherein $R_2$ represents a hydrogen atom, a lower alkoxy, formyl, lower alkanoyl, phenyl group, or a group of the formula, $—(CH_2)_nCOOR_3$, wherein $R_3$ represents a hydrogen atom, or a lower alkyl, phenyl, benzyl, anisyl or lower alkoxycarbonylmethyl group, and n represents an integer of 0 to 2, or a pharmaceutically acceptable salt thereof.

9. The anti-ulcer agent of claim 8 which is (2'-benzyloxycarbonyl)phenyl trans-4-guanidinomethylcyclohexanecarboxylate hydrochloride.

10. An anti-ulcer agent which comprises a compound of the formula,

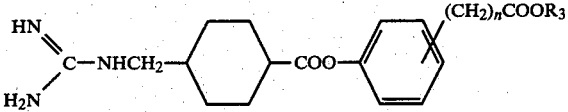

wherein $R_3$ represents a hydrogen atom or a lower alkyl, phenyl, benzyl, anisyl or lower alkoxycarbonylmethyl group, and n represents an integer of 0 to 2, or a pharmaceutically acceptable salt thereof.

11. The anti-ulcer agent of claim 10 which is (2'-benzyloxycarbonyl)phenyl trans-4-guanidinomethylcyclohexanecarboxylate hydrochloride monohydrate.

* * * * *